United States Patent [19]

Khandelwal et al.

[11] Patent Number: 5,252,598

[45] Date of Patent: Oct. 12, 1993

[54] LABDANE DERIVATIVES, A PROCESS FOR THEIR PREPARATION, AND THEIR USE AS MEDICAMENTS

[75] Inventors: Yatendra Khandelwal; Greta Moraes; Bansi Lal; Vijay A. Aroskar; Alihussein N. Dohadwalla, all of Bombay, India; Richard H. Rupp, Königstein/Taunus, Fed. Rep. of Germany

[73] Assignee: Hoechst Aktiengesellschaft, Frankfurt am Main, Fed. Rep. of Germany

[21] Appl. No.: 879,108

[22] Filed: May 4, 1992

Related U.S. Application Data

[63] Continuation of Ser. No. 579,193, Sep. 7, 1990, abandoned, which is a continuation of Ser. No. 277,174, Nov. 29, 1988, abandoned.

[30] Foreign Application Priority Data

Dec. 1, 1987 [DE] Fed. Rep. of Germany ....... 3740625

[51] Int. Cl.$^5$ ..................... A61K 31/35; C07D 311/92
[52] U.S. Cl. .................... 514/455; 549/389; 548/525; 548/311.4; 546/269; 546/196; 544/375; 544/268; 544/150; 544/50; 540/596; 514/422; 514/397; 514/320; 514/337; 514/265; 514/232.8; 514/228.2; 514/253; 514/212

[58] Field of Search ............... 549/389; 548/525, 336; 546/269, 196; 540/596; 514/455, 422, 397, 320, 337, 265, 232.8, 228.2, 253, 212; 544/268, 375, 150, 60

[56] References Cited

U.S. PATENT DOCUMENTS

4,517,200  5/1985  Kreutner et al. .................. 514/455

OTHER PUBLICATIONS

Bhat et al., Tetrahedron Letters, No. 19, pp. 1669-1672 (1977).

Primary Examiner—Nicky Chan
Attorney, Agent, or Firm—Finnegan, Henderson, Farabow, Garrett & Dunner

[57] ABSTRACT

The present invention relates to labdane-derivatives of the formula

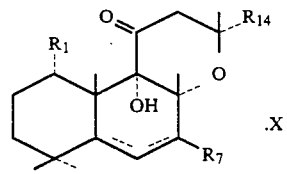

a process for their preparation and the use of these substances as medicaments, preferably as medicaments having a positive ionotropic effect, an effect of lowering intraocular pressure and lowing blood pressure.

11 Claims, No Drawings

LABDANE DERIVATIVES, A PROCESS FOR THEIR PREPARATION, AND THEIR USE AS MEDICAMENTS

This application is a continuation of application Ser. No. 07/579,193 filed Sep. 7, 1990, now abandoned, which is a continuation of application Ser. No. 07/277,174 filed Nov. 29, 1988, abandoned.

The present invention relates to new derivatives of polyhydroxylated labdanes and their physiologically utilizable salts, to a process for their preparation, and to their use as medicaments.

Polyhydroxylated labdanes and their derivatives have already been described in: German Offenlegungsschriften Nos. 2,557,784, 2,640,275 and 2,654,796; Tetrahedron Letters No. 19, pages 1669-1672 (1977); J. Chem. Soc., Perkin Trans. 1, 767 (1982), and in European Patent Applications EP-A 0,217,372, EP-A 0,191,166 and EP-A 0,193,132.

As a consequence of the pharmacological properties of the polyhydroxylated labdanes and their derivatives they are suitable for the treatment of cardiovascular disorders, high blood pressure, glaucoma, allergies and asthma, and they act as immunomodulators and act to stimulate adenylate cyclase.

The polyhydroxylated labdanes according to the invention are neither described in the publications mentioned as state of the art nor are they obvious from the latter. Compounds of the state of the art, which in some cases are structurally related to the compounds according to the invention, are the derivatives which have an aminoacyloxy group or hydroxyacyloxy group in the 7-position.

The essential difference between the compounds according to the invention and those of the state of the art is that, in the compounds according to the present invention, one of the bonds between the carbon atoms in the 5- and 6-positions or in the 6- and 7-positions is a double bond, or both bonds are single bonds, in the latter case the 6-substituent being only hydrogen. Surprisingly, these structural changes alter the pharmacological profile of the compounds, resulting in these compounds being more suitable for the treatment of diseases with heart failure, such as congestive cardiomyopathy and related indications, for the treatment of hypertension and for the treatment of elevated intraocular pressure.

Hence the present invention relates to new derivatives of polyhydroxylated labdanes of the formula I

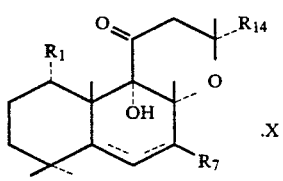

in which
R$_1$ denotes OH, O-alkyl or a group of the formula II

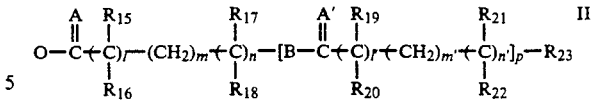

in which A and A' represent oxygen or sulfur, B represents —CH$_2$—, oxygen sulfur or —NH—, R$_{15}$-R$_{23}$ represent hydrogen, alkyl, aryl, aralkyl, hydroxyl, acyl, alkoxy, mercapto, halogen or a group of the formula NR$_{24}$R$_{25}$, in which R$_{24}$ and R$_{25}$ denote, if they are identical, hydrogen, alkyl, substituted alkyl, aryl or aralkyl, or, if R$_{24}$ represents hydrogen, R$_{25}$ denotes alkyl, substituted alkyl, cycloalkyl, aralkyl, aryl, a heterocyclic radical, amino, dialkylamino, alkylamino, arylamino, aralkylamino, hydroxyl, mercapto, acyloxy, acyl, carbamoyl, carboxyalkyl, carbalkoxyalkyl or dialkyLaminoalkyl, or, if R$_{24}$ represents alkyl, R$_{25}$ denotes substituted alkyl, cycloalkyl, aryl, aralkyl or dialkylaminoalkyl, or R$_{24}$ and R$_{25}$ represent, together with the nitrogen atom to which they are bonded, a heterocyclic radical which can have one or more hetero atoms and be optionally substituted once or several times by alkyl, aryl, hydroxyalkyl, halogen, hydroxy, alkoxy or other heterocyclic groups, with the proviso that the radical of the formula II contains at least three of the substituents R$_{15}$-R$_{23}$, at least one of the three substituents having a hetero atom of the group comprising N, O or S, and L, m, n, l', m', n' and p each denote 0 or an integer from 1 to 10, or R$_1$ represents a radical of the formulae

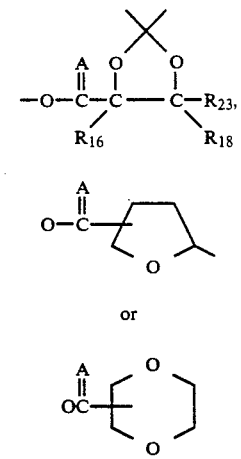

in which A, R$_{16}$-R$_{18}$ and R$_{23}$ have the same meaning as indicated above,
R$_7$ denotes OH, O-alkyl or a radical of the formula II

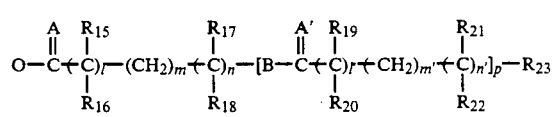

or of the formulae

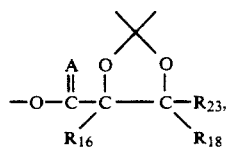

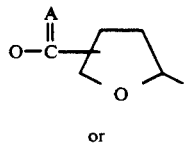

or

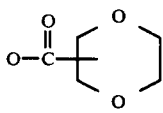

in which A, A', l, m, n, l', m', n', p and $R_{15}$–$R_{23}$ have the same meaning as indicated above, denotes vinyl, ethyl, cyclopropyl, $CHOHCH_2OH$, $CH_2OH$ or the radical

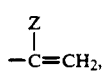

in which Z represents halogen such as chlorine, bromine or fluorine, is present or absent, and when X is present, the formula I represents a pharmacologically utilizable salt, and the dotted lines denote that a double bond can be present in either the 5,6- or the 6,7-position, with the proviso that $R_1$ and $R_7$ are not both OH groups.

A preferred group of compounds of the present invention are compounds of the formula I in which:
$R_1$ denotes OH,
$R_7$ denotes a group contributing to the radical of the formula II described above, represented by the formula II'

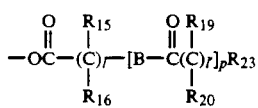

in which l, B, $R_{15}$, $R_{16}$, $R_{19}$, $R_{20}$ and $R_{23}$ have the abovementioned meaning, or a radical of the formula

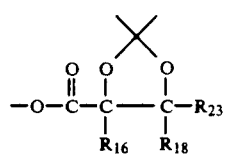

in which $R_{16}$, $R_{18}$ and $R_{23}$ represent hydrogen, $R_{14}$ denotes vinyl, ethyl, cyclopropyl, $CHOHCH_2OH$, $CH_2OH$ or

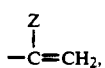

in which Z represents halogen such as chlorine, bromine or fluorine, and a double bond is located in the 5,6-position, with the proviso that in the radical II'

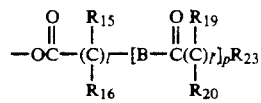

at least one of the substituents $R_{15}$, $R_{16}$, $R_{19}$, $R_{20}$, $R_{23}$ or B contains an atom from the group comprising N, O or S.

A second group of preferred compounds are those where $R_1$ and $R_7$ each denote OH, OAc or a radical of the formula II''

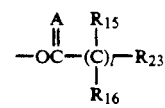

$R_{14}$ denotes vinyl, ethyl, cyclopropyl, $CHOHCH_2OH$ or

in which Z represents halogen such as chlorine, bromine or fluorine, and a double bond is located in the 5,6-position, with the proviso that at least one of the substituents $R_1$ and $R_7$ denotes the radical II''

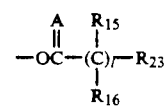

in which A, L, $R_{15}$, $R_{16}$ and $R_{23}$ have the abovementioned meaning, but at least one of the substituents $R_{15}$, $R_{16}$ and $R_{23}$ contains an atom from the group comprising N, O or S.

Suitable examples for the definition of alkyl for the substituents $R_{15}$–$R_{25}$ are straight-chain or branched alkyl radicals having up to 6, and preferably up to 4, carbon atoms, for example methyl, ethyl, isopropyl, t-butyl and n-butyl.

Suitable examples of substituted alkyl groups in the meaning of $R_{24}$ and $R_{25}$ are hydroxy-$C_1$–$C_6$-alkyl such as hydroxyethyl, carboxy-$C_1$–$C_6$-alkyl such as carboxyethyl, and carb-$C_1$–$C_6$-alkoxyalkyl such as carbethoxyethyl.

Suitable examples of cycloalkyl groups in the meaning of $R_{24}$ and $R_{25}$ are $C_3$–$C_7$-cycloalkyl groups, in particular cyclopentyl, cyclohexyl or cycloheptyl.

Suitable examples of aralkyl groups in the meaning of $R_{24}$ and $R_{25}$ are phenylalkyl groups, in particular phenyl-$C_1$–$C_3$-alkyl, for example the benzyl group, in which the phenyl group can be substituted by one or more substituents such as halogen, $C_1$–$C_3$-alkyl, $C_1$–$C_3$-alkoxy, nitro or trifluoromethyl.

A suitable example of aryl groups in the meaning of $R_{24}$ and $R_{25}$ is the phenyl group, which can be substituted by one or more substituents such as halogen, $C_1$–$C_3$-alkyl, $C_1$–$C_3$-alkoxy, nitro or trifluoromethyl.

Suitable examples of acyl groups in the meaning of $R_{15}$–$R_{23}$ and $R_{25}$ are $C_1$–$C_6$-alkanoyl, $C_2$–$C_6$-alkenoyl, aroyl, aryl-$C_1$–$C_6$-alkanoyl or a heteroaroyl group having up to 10 carbon atoms, in which one or more carbon atoms can be replaced by oxygen, nitrogen and/or sulfur.

Examples of alkanoyl groups of this type are formyl, acetyl, propionyl, butyryl, isobutyryl, valeryl, palmityl or bromoisobutyryl, preferably formyl, acetyl or propionyl. The alkanoyl groups can contain one or more double bonds, for example acryloyl, stearoyl or oleoyl. The alkanoyl groups can contain one or more triple bonds. They can, in addition, contain one or more double bonds. An example of such alkynoyl groups is propiolyl. Aroyl groups are represented by, for example, benzoyl, in which the phenyl group can be substituted by one or more substituents such as $C_1$–$C_3$-alkyl, $C_1$–$C_3$-alkoxy, halogen, nitro or trifluoromethyl. Examples of aralkanoyl and heteroaroyl groups are phenylacetyl and pyridine-3-carbonyl, respectively.

Dialkylaminoalkyl groups are to be understood to be those in which each of the alkyl groups contains 1 to 6 carbon atoms, such as diethylaminoethyl.

Where $R_{24}$ and $R_{25}$, together with the nitrogen atom to which they are bonded, represent a heterocycle, preference is given to piperidine, pyrrolidine, morpholine, piperazine, thiomorpholine, imidazole or theophylline, each of which can be substituted once or several times by $C_1$–$C_4$-alkyl, $C_1$–$C_4$-alkoxy, aryl, aryl-$C_1$–$C_4$-alkyl, hydroxyl, amino, or substituted alkyl or amino.

Suitable examples of salts of the compounds of the invention with inorganic or organic acids are hydrochloride, hydrobromide, sulfate, phosphate, acetate, oxalate, tartrate, citrate, maleate or fumarate.

In the formulae depicted here, the various substituents are shown as connected to the labdane nucleus in one of two modes of representation: a full line (—) which indicates a substituent in the β-orientation (i.e. above the plane of the molecule), and a broken line (--) which indicates a substituent in the α-orientation (i.e. below the plane of the molecule). All the formulae are drawn in such a way that they depict the compounds in their absolute stereochemical configuration. Since the starting materials having a labdane nucleus are naturally occurring or are derived from naturally occurring materials they have, as do the final products, a labdane nucleus existing in the single absolute configuration depicted here. However, the process of the present invention is also meant for application to the synthesis of labdanes of the racemic series.

In addition to the optical centers of the labdane nucleus, the substituents thereon may also have chiral centers which contribute to the optical properties of the compounds of the present invention and after a means for their separation by conventional methods, for example by the use of optically active acids. A wavy line (~) connecting a group to a chiral center indicates that the stereochemistry of the center is unknown, i.e. the group may be present in any of the possible orientations. The present invention embraces all the optical isomers and racemic forms of the compounds of the present invention when such compounds have chiral centers in addition to those of the subdane nucleus.

Some of the new derivatives of polyoxygenated labdanes according to the invention are listed in Table I.

TABLE I

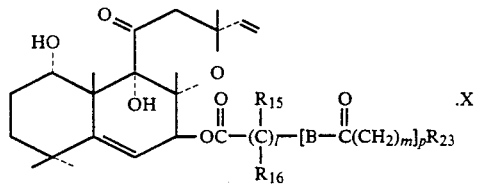

Ia

| 1 | $R_{15}$ | $R_{16}$ | p | B | m' | $R_{23}$ | X | m.p. (°C.) |
|---|---|---|---|---|---|---|---|---|
| 2 | H | OH | 0 | — | 0 | H | — | 182–184 (R. config.) |
| 0 | — | — | 0 | — | 0 | $CH_3$ | — | 160–162 |
| 1 | H | H | 1 | 0 | 0 | H | — | 116–118 |
| 1 | H | H | 0 | — | 0 | OH | — | 156 |
| 1 | H | H | 1 | 0 | 1 | ⟨N-piperidinyl⟩ | — | 108–110 |
| 1 | H | H | 1 | 0 | 1 | ⟨N-piperidinyl⟩ | HCl | 217–219 |
| 1 | H | H | 1 | 0 | 1 | ⟨N-morpholinyl⟩ | HCl | 192–194 (Z) |
| 1 | H | H | 1 | 0 | 1 | $N(CH_3)_2$ | HCl | 209 |
| 1 | H | H | 1 | 0 | 1 | $N(C_2H_5)_2$ | $HCl \cdot H_2O$ | 130–133 |

TABLE I-continued

Ia

| l | R15 | R16 | p | B | m' | R23 | X | m.p. (°C.) |
|---|-----|-----|---|---|----|----|---|------------|
| 1 | H | H | 1 | 0 | 1 | (morpholine) | HCl.H2O | 138–140 |
| 1 | H | H | 1 | 0 | 1 | (N-methylpiperazine) | 2HCl.H2O | 177–180 |
| 1 | H | H | 1 | 0 | 1 | (4-hydroxy-4-phenylpiperidine) | HCl.0,5H2O | 157–160 |
| 1 | H | H | 1 | 0 | 2 | N(CH3)2 | HCl.0,5H2O | 178 |
| 1 | H | H | 1 | 0 | 2 | (morpholine) | HCl | 189–190 |
| 1 | H | H | 1 | 0 | 2 | (N-methylpiperazine) | 2HCl.H2O | 230 |

Compound of the formula

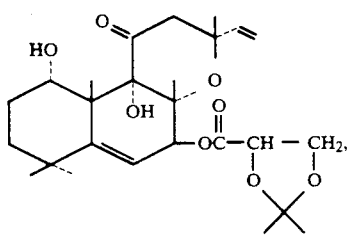

Melting point 151–153° C.
(R configuration)

Tables II and III list compounds corresponding to the second group of preferred compounds defined above having the formulae Ib and Ic, respectively.

TABLE II

Ib

| R1 | l | R15 | R16 | R23 | X | m.p. (°C.) |
|----|---|-----|-----|-----|---|------------|
| OCOCH2N(piperidine) | 0 | — | — | CH3 | HCl.0,5H2O | 123–125 |
| OH | 0 | — | — | NH2 | 0,5H2O | 233–234 |
| OH | 0 | — | — | NHCH3 | — | 117–118 |
| OH | 0 | — | — | NH(CH2)2CH3 | — | 240 |
| OH | 0 | — | — | NHC6H5 | — | 217 |
| OH | 0 | — | — | N(CH3)2 | — | 113–114 |

TABLE II-continued

Ib

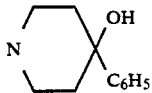

| R1 | l | R15 | R16 | R23 | X | m.p. (°C.) |
|---|---|---|---|---|---|---|
| OH | 0 | — | — | (pyrrolidine) | 0,5H2O | 238 |
| OH | 0 | — | — | (piperidine) | — | 199–200 |
| OH | 0 | — | — | (morpholine) | — | 192 |
| OH | 0 | — | — | (N-methylpiperazine) | 1,25HCl.2H2O | 193–195 |
| OH | 0 | — | — | (N-phenylpiperazine) | HCl | 202–204 |

TABLE III

Ic

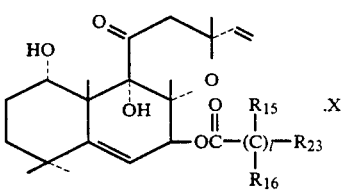

| l | R15 | R16 | R23 | X | m.p. (°C.) |
|---|---|---|---|---|---|
| 1 | H | H | NMe2 | HCl | 243 |
| 1 | H | H | NEt2 | HCl | 210–211 |
| 1 | H | H | (pyrrolidine) | HCl | 220–221 |
| 1 | H | H | (piperidine) | HCl | 227–228 |
| 1 | H | H | (azepane) | HCl | 215–216 |
| 1 | H | H | (morpholine) | HCl.H2O | 193–195 |

TABLE III-continued

Ic

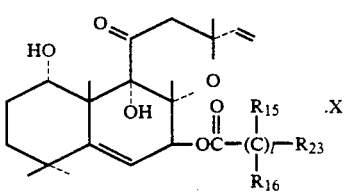

| l | R15 | R16 | R23 | X | m.p. (°C.) |
|---|---|---|---|---|---|
| 1 | H | H | (N-methylpiperazine) | 2HCl.H2O | 220–223 |
| 1 | H | H | (thiomorpholine) | HCl | 203–204 |
| 1 | H | H | (4-methylpiperidine) | HCl | 228–230 |
| 1 | H | H | (3-methylpiperidine) | HCl.0.5H2O | 219–220 |

TABLE III-continued

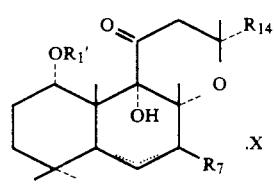

| l | R$_{15}$ | R$_{16}$ | R$_{23}$ | X | m.p. (°C.) |
|---|---|---|---|---|---|
| 1 | H | H | ![N-piperidine-OH-Ph] | HCl.H$_2$O | 194–195 |
| 1 | H | H | ![N-morpholine-diCH3] | — | 191–192 |
| 2 | H | H | NMe$_2$ | — | 163–164 |
| 2 | H | H | NEt$_2$ | — | 153–154 |
| 2 | H | H | ![piperidine] | — | 169–170 |
| 2 | H | H | ![morpholine] | — | 168–169 |
| 2 | H | H | ![N-methylpiperazine] | — | 154–155 |
| 3 | H | H | NMe$_2$ | — | 177–178 |
| 3 | H | H | NEt$_2$ | — | 149–150 |
| 3 | H | H | ![piperidine] | 0.5H$_2$O | 185–186 |
| 3 | H | H | ![morpholine] | — | 183–186 |
| 3 | H | H | ![N-methylpiperazine] | — | 196–197 |
| 3 | H | H | ![piperidine-OH-Ph] | — | 132–133 |
| 4 | H | H | NMe$_2$ | — | 172–173 |
| 4 | H | H | ![piperidine] | — | 166–169 |
| 4 | H | H | ![morpholine] | — | 168–169 |
| 4 | H | H | ![N-methylpiperazine] | — | 161–162 |
| 1 | H | CH$_3$ | ![piperidine] | HCl | 225–226 |

The invention also relates to a process for the preparation of new derivatives of polyhydroxylated labdanes of the general formula I.

The process comprises reaction of a compound of the formula I'

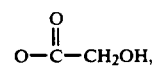

in which

R$_1$' represents H and R$_7$ represents OH or the group $$O-\overset{O}{\underset{\|}{C}}-CH_2OH,$$

or R$_1$' represents a protective group for a hydroxyl group, such as, for example, the t-butyldimethylsilyl group, and R$_7$ represents OH or the group $$O-\overset{O}{\underset{\|}{C}}-CH_2OH,$$

a) with a compound of the formula III

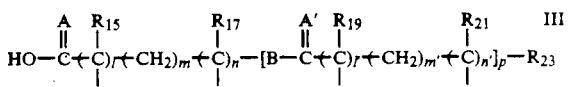

in which R$_{15}$–R$_{22}$, A, A', B, l, m, n, l', m', n' and p have the abovementioned meanings, and R$_{23}$ represents a halogen atom such as Cl, Br or I, or the group OW, W representing aryl-C$_1$-C$_6$-alkyl or aryl, to give a compound of the formula I in which $R_1$ and/or $R_7$ denotes a radical of the formula II $$O-\overset{A}{\underset{R_{16}}{\overset{\|}{C}}}\overset{R_{15}}{\underset{|}{\overset{|}{C}}})_l-(CH_2)_m-\overset{R_{17}}{\underset{R_{18}}{\overset{|}{C}}})_n-[B-\overset{A'}{\underset{R_{20}}{\overset{\|}{C}}}\overset{R_{19}}{\underset{|}{\overset{|}{C}}})_{l'}-(CH_2)_{m'}-\overset{R_{21}}{\underset{R_{22}}{\overset{|}{C}}})_{n'}]_p-R_{23} \quad \text{II}$$

in which $R_{15}$–$R_{22}$, A, A', B, l, m, n, l', m', n' and p have the said meanings, and $R_{23}$ represents a halogen atom or an O-aryl-$C_1$-$C_6$-alkyl or aryl radical, and elimination by customary methods of $R_1'$ if it represents a protective group, or b) with a compound of the formula $$\text{HOC—CH — CH}_2$$
$$\overset{\|}{O} \quad \overset{|}{\underset{O}{\diagdown}} \quad \overset{|}{\underset{O}{\diagup}}$$
$$\times$$

to give a compound of the formula I in which one of the two substituents $R_1$ and $R_7$ represents the radical $$\text{OC—CH — CH}_2$$
$$\overset{\|}{O} \quad \overset{|}{\underset{O}{\diagdown}} \quad \overset{|}{\underset{O}{\diagup}}$$
$$\times$$

where appropriate c) treatment of a compound of the formula I in which one of the substituents $R_1$ and $R_7$ represents the OH group, and the other represents a radical of the formula $$\text{OC—CH — CH}_2$$
$$\overset{\|}{O} \quad \overset{|}{\underset{O}{\diagdown}} \quad \overset{|}{\underset{O}{\diagup}}$$
$$\times$$

with an organic acid, resulting in a compound of the formula I in which either $R_1$ or $R_7$ represents the radical $$\begin{array}{c}-O-C-CH-CHOH\\ \|\ \ |\\ O\ \ OH\end{array}$$

and the other represents the OH group, or d) reaction of a compound of the formula I in which one of the substituents $R_1$ and $R_7$ represents the radical $$-OCCH_2R_{23},$$
$$\overset{\|}{O}$$

$R_{23}$ denoting halogen, and the other represents the OH group, with sodium formate to give a compound of the formula I in which one of the substituents $R_1$ and $R_7$ represents the radical —OCOCH$_2$—O—CHO, e) where appropriate reaction of the compound obtained in step c) with aluminum oxide to give a compound of the formula I in which one of the substituents $R_1$ and $R_7$ represents the radical —OCOCH$_2$OH, f) where appropriate initial acylation, by customary methods, of the compound of the formula I obtained in step d), and subsequent reaction of the resulting compound with an amine of the formula $HNR_{24}R_{25}$, in which $R_{24}$ and $R_{25}$ have the abovementioned meanings, to give a compound of the formula Ia in which one of the substituents $R_1$ and $R_7$ denotes the OH group, and the other denotes a radical of the formula $$\begin{array}{c}O\quad\quad\quad\quad O\\ \|\quad\quad\quad\quad\|\\ OC-CH_2-O-C-(CH_2)_{m'}R_{23}\end{array}$$

in which m' has the abovementioned meaning, and $R_{23}$ represents the group —$NR_{24}R_{25}$, $R_{24}$ and $R_{25}$ having the abovementioned meanings, g) where appropriate, initial reaction of a compound of the formula I', in which $R_1'$ denotes a protective group for a hydroxyl group, and $R_7$ denotes OH, with a compound of the formula IV in which T denotes oxygen or sulfur, subsequent addition of an amine of the formula $HNR_{24}R_{25}$ to the reaction mixture, or by treatment of a compound of formula I' with potassium cyanate and trifluoroacetic acid and finally elimination of the protective group in the 1-position in a known manner, resulting in a compound of the formula I in which $R_1$ denotes OH, and $R_7$ denotes a radical of the formula —$OCONR_{24}R_{25}$, in which $R_{24}$ and $R_{25}$ have the abovementioned meanings, h) where appropriate acylation of a compound of the formula I in which $R_1'$ denotes a protective group for a hydroxyl group, and $R_7$ denotes OH, with a compound of the formulae

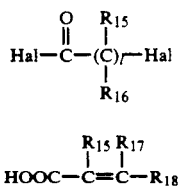

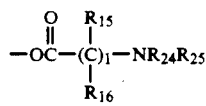

in which Hal denotes a halogen atom, and $R_{15}$, $R_{17}$ and $R_{18}$ each represent hydrogen, optionally substituted $C_1$–$C_6$-alkyl, aryl or aryl-$C_1$–$C_6$-alkyl, reaction of the resulting reaction product with an amine of the formula $HNR_{24}R_{25}$, in which $R_{24}$ and $R_{25}$ have the abovementioned meanings, and finally elimination of the protective group in the 1-position, resulting in a compound of the formula I in which $R_1$ represents the OH group, and $R_7$ represents a radical of the formula $$-\underset{\text{O}}{\overset{\text{O}}{\text{C}}}-\underset{R_{16}}{\overset{R_{15}}{\text{(C)}_l}}-NR_{24}R_{25}$$

in which $R_{15}$, $R_{16}$, $R_{24}$, $R_{25}$ and L have the abovementioned meanings.

The acylation in steps a) and b) is carried out in organic solvents such as ethyl acetate or dichloromethane in the presence of a carbodiimide, such as dicyclohexylcarbodiimide, and of a catalyst, such as a tertiary amine. Examples of tertiary amines which may be mentioned are 4-dimethylaminopyridine or N,N-dimethylaniline, preference being given to 4-dimethylaminopyridine. The temperature at which the acylation is carried out is not critical, but it is preferable to carry out the reaction at a temperature in the range 0°–50° C. It is most preferable to carry out the acylation reaction at 27° C.–30° C. The reaction is carried out for a period of 16–24 hours. The most preferred period is 16 hours. The compounds of the formula I are isolated from the reaction mixture in a known manner. For example, the reaction mixture is filtered and the filtrate is washed with bicarbonate solution and water, dried over anhydrous sodium sulfate and then concentrated. The resulting residue is purified by flash chromatography and then recrystallized from organic solvents such as petroleum ether-/ethyl acetate mixture.

The derivatization of compounds of the formula I in which one of $R_1$ and $R_7$ represents hydroxyl, and the other of $R_1$ and $R_7$ represents a group of the formula

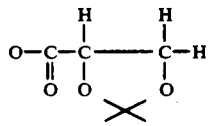

is carried out in a manner known to the expert, by treatment with organic acids such as p-toluenesulfonic acid or acetic acid in alkanols, such as methanol, as solvent and at room temperature, in order to obtain the corresponding derivatives of the formula I in which $R_1$ or $R_7$ is a radical of the formula

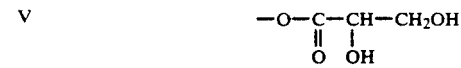

For the derivatization of compounds of the formula I in which one of the substituents $R_1$ and $R_7$ is

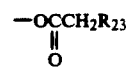

and $R_{23}$ represents halogen, they are treated with sodium formate in an organic solvent such as hexamethylphosphoramide at room temperature, in order to obtain the corresponding formyl derivative of the formula I in which $R_1$ or $R_7$ represents

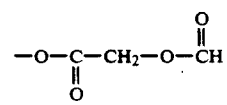

The latter compound is further reacted by treatment with aluminum oxide to give a compound of the formula I in which $R_1$ or $R_7$ represents the hydroxyacetoxy group O—CO—$CH_2$OH. The latter compound is further reacted by acylation with carboxylic acids of the formula V

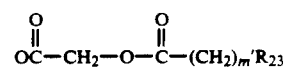

and subsequent treatment with an amine of the formula $HNR_{24}R_{25}$, in which $R_{24}$ and $R_{25}$ are as above, to give a compound of the formula I.

The process for the preparation of compounds of the formula Ib (Table II) comprises initial reaction of a compound of the formula I' with a compound of the formula IV

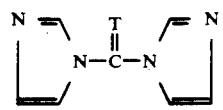

in which T is oxygen or sulfur, and then addition of an amine of the formula $HNR_{24}R_{25}$, in which $R_{24}$ and $R_{25}$ are as defined above, to the reaction mixture, in organic solvents such as ethyl acetate, at room temperature and with maintenance of an inert atmosphere by, for example, nitrogen gas, and stirring for a total period of 26 to 36 hours, or by the treatment of a compound of formula I' with potassium cyanate and trifluoroacetic acid. The removal of the protective group, for example alkylsilyl, in the 1-position and the isolation and purification of the compound of the formula I from the reaction mixture are carried out in a known manner.

The process for the preparation of compounds of the formula Ic in which $R_7$ represents the radical

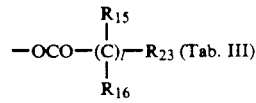

comprises two stages. The first stage comprises the acylation of compounds of the formula I' using an equimolar amount of a haloalkanoyl halide of the formula V

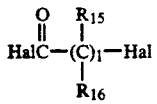

in which $R_{15}$–$R_{16}$ and l are as defined above, and Hal represents halogen such as chlorine or bromine, in the presence of a base such as pyridine or triethylamine, or acylation using a carboxylic acid of the formula VI

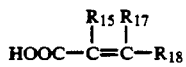

in which $R_{15}$–$R_{16}$ and $R_{18}$ represent hydrogen, alkyl, substituted alkyl, aryl or aralkyl, in the presence of dicyclohexylcarbodiimide and 4-dimethylaminopyridine in organic solvents. The second stage comprises reaction of the acylated product with amines of the formula $HNR_{24}R_{25}$ in which $R_{24}$ and $R_{25}$ have the same meaning as described above.

The reaction in the first stage can be carried out at temperatures of 0° C. to room temperature and in solvents such as aromatic hydrocarbons, such as benzene or toluene, or ethers, such as dioxane or tetrahydrofuran, or halogenated hydrocarbons, such as chloroform or methylene chloride, ethylacetate, dimethylformamide. The reaction is carried out for 0.5 to 24 hours. The product which is formed is isolated by dilution of the reaction mixture with the solvent which is used, washing successively with water, dilute hydrochloric acid, water, sodium bicarbonate and water, and drying over anhydrous sodium sulfate and, finally, concentration in vacuo. The resulting residue is a mixture of compounds and is, where appropriate, used without purification in the second stage of the reaction with amines of the formula $HNR_{24}R_{25}$.

The second stage of the process is carried out at temperatures in the range between room temperature and 150° C., for 0.5 to 6 hours, with or without solvents. The solvents which are used are aromatic hydrocarbons, such as benzene or toluene, ethers, such as tetrahydrofuran or dioxane, or halogenated hydrocarbons, such as chloroform or methylene chloride. The product is isolated from the reaction mixture by concentration of the reaction mixture, followed by extraction using an organic solvent, washing of the extract with water, drying of the organic layer over anhydrous sodium sulfate, concentration of the extract, and purification of the resulting residue by either crystallization or chromatography.

The starting material for the preparation of the compounds of the invention is, for example, 8,13-epoxy-1α,9α,7β-trihydroxylabda-5,14-dien-11-one, of the formula I in which $R_1$ and $R_7$ each denotes the OH group, and $R_{14}$ denotes the vinyl group. It can be prepared by methods already described in the literature. It can also be prepared starting from forskolin, in which initially the 1-hydroxyl group is protected by acetyl or t-butyl-dimethylsilyl by customary processes, and which is then treated with thionyl chloride and pyridine in an anhydrous solvent, for example dichloromethane, at 0° C.

The reaction mixture is stirred at room temperature for 18 hours, and then the product of the formula VIII

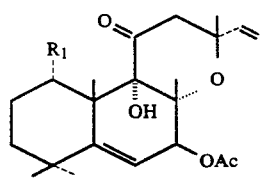

in which $R_1$ represents a protective group for the OH group, for example —OAc or —OSi(CH$_3$)$_2$C(CH$_3$)$_3$, is isolated. Treatment of the compound with non-aqueous alkali, for example NaOH in methanol, at room temperature with stirring and for a period of 3 hours results in a compound of the formula IX

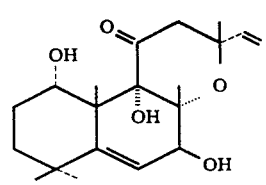

which can be used as starting compound for further reactions.

The compounds of the invention obtained as free bases can, if desired, be converted into an inorganic acid addition salt such as hydrochloride, hydrobromide, sulfate or phosphate, or into an organic acid addition salt such as the salt of formic acid, acetic acid, fumaric acid, maleic acid, citric acid, tartaric acid, lactic acid or methane-sulfonic acid.

The compounds of the present invention and their salts have the pharmacological properties attributed in the literature to the class of polyhydroxylated labdanes and their derivatives. However, they exhibit in a more specific manner a selective positive inotropic activity, antihypertensive activity and reduction of the intraocular pressure. This is shown by the following pharmacological experiments.

POSITIVE INOTROPIC ACTIVITY

The following method was used:

Guineapigs of both sexes and weighing 400 g were sacrificed, and the heart was removed and placed in Ringer's solution at room temperature. Both the left and the right atria were then isolated and fixed in an organ holder, and the preparation was placed in an organ bath containing Ringer's solution and maintained at a temperature of 32° C. Carbogen (95% $O_2$ and 5% $CO_2$) was then bubbled through the organ bath. The compound to be tested is dissolved directly in water together with a stoichiometric amount of 0.1N HCL or a salt thereof to give a solution of known concentration and the latter is added to the bath. The contractility of the atrium is recorded for 7 to 10 minutes on a Nihon Kohden 4-channel pen recorder with an isometric strain gage. The activity is expressed on the basis of the resulting data as the $EC_{50}$.

The results obtained for representative compounds of the invention are given in the table which follows.

| $R_7$ | X | Guinea pig atrium $EC_{50}$ μg/ml |
|---|---|---|
| Compound (structure with HO, OH, OR₇, O) .X | | |
| $COCH_3$ | — | 0.028 |
| $COCH_2OCHO$ | — | 0.024 |
| (R) $COCH-CH_2OH$ $\quad\;$ OH | — | 0.0008 |
| $CONHCH_3$ | — | 0.051 |
| CON-morpholine | — | 0.3 |
| CON-(N-methylpiperazine) | HCl | 0.24 |
| Compound (structure) .HCl | | |
| $COCH_2N$-(2,6-dimethylmorpholine) | | 0.079 |
| $CO(CH_2)_2N$-piperidine | | 0.28 |
| $CO(CH_2)_2N$-(N-methylpiperazine) | | 0.30 |
| $CO(CH_2)_3NEt_2$ | | 0.037 |
| $CO(CH_2)_3N$-(N-methylpiperazine) | | 0.12 |
| $CO(CH_2)_4NMe_2$ | | 0.755 |
| $CO(CH_2)_4NMe_2$ | | 0.615 |

| $R_7$ | X | Guinea pig atrium $EC_{50}$ μg/ml |
|---|---|---|
| $CO(CH_2)_4N$-morpholine | | 0.17 |
| Compound (structure with HO, OH, OR₇, O) .X | | |
| $COCH_2N$-piperidine | HCl | 0.072 |
| $COCH_2N(C_2H_5)_2$ | HCl | 0.72 |
| $COCH_2N$-thiomorpholine | HCl | 0.14 |
| $COCH_2N$-(4-hydroxy-4-phenylpiperidine) | HCl | 0.3 |
| $CO(CH_2)_3N(CH_3)_2$ | — | 0.058 |
| $COCH_2OCOCH_2NMe_2$ | HCl | 0.8 |
| $COCH_2OCOCH_2NEt_2$ | HCl.H₂O | 0.018 |
| $COCH_2OCOCH_2N$-piperidine | HCl | 3.0 |
| $COCH_2OCOCH_2N$-morpholine | HCl | 1.0 |
| $COCH_2OCOCH_2N$-(2,6-dimethylmorpholine) | HCl.H₂O | 0.72 |
| $COCH_2OCOCH_2N$-(N-methylpiperazine) | 2HCl.H₂O | 0.44 |
| $COCH_2OCO(CH_2)_2N$-(N-methylpiperazine) | 2HCl.H₂O | 1.0 |

REDUCTION IN INTRAOCULAR PRESSURE

MEASUREMENT OF THE INTRAOCULAR PRESSURE IN CONSCIOUS RABBITS

For this experiment rabbits of both sexes and weighing 2 to 3 kg are used. The intraocular pressure (IOP) is measured with a Schioetz tonometer after corneal anesthesia with 2% strength novocaine solution. A compound according to the invention, or a salt thereof, is suspended in a concentration of 2% in 0.5% CMC. After the baseline value has been determined, 100 µl of the suspension of the test compound are instilled in a concentration of 2% into one of the eyes, white the other receives vehicle. The IOP is measured at defined time intervals, i.e. after 0.5, 1, 2, 3, 4 and 5 hours. The percentage reduction in the IOP is calculated using the baseline value.

The results obtained for representative compounds of the invention tested in this model are given in the table which follows:

Compound

| $R_7$ | X | Dose percentage | % decrease in IOD | Duration (mins) |
|---|---|---|---|---|
| (R) —CO—CH—CH$_2$OH  <br>        \|  <br>       OH | — | 0.25 | 35.0 | >360 |
| \multicolumn{5}{l}{Reduction of IOD} |
| CONH$_2$ | — | 1.00 | 30.0 | >360 |
| CONHCH$_3$ | — | 1.00 | 24.0 | >360 |
| \multicolumn{5}{l}{Activity of decreasing IOD} |
| CONH(CH$_2$)$_3$CH$_3$ | — | 1.00 | 27.0 | >360 |
| CON⟨O⟩ (morpholine) | — | 1.00 | 26.0 | 240 |
| COCH$_2$N⟨O⟩ | — | 2.00 | 20.3 | 360 |
| COCH$_2$N⟨N—CH$_3$⟩ | HCl | 2.00 | 23.9 | 360 |

ANTIHYPERTENSIVE EFFECT

Blood pressure in cats:

Cats of both sexes and weighing 3 to 4 kg were anesthetized with ether and maintained under chloralose anesthesia (70 mg/kg i.v.). Cannulas were placed in the femoral artery and in the femoral vein to record the blood pressure and to administer the medicament, respectively. The blood pressure in the femoral artery was recorded using a Statham P 23 Db pressure transducer on a Nihon-Kohden pen recorder for physiological purposes. The compound to be tested was dissolved, if a salt, in distilled water, otherwise in propylene glycol and administered intravenously. The fall in blood pressure and the duration of the hypotensive activity were determined.

The results obtained for representative compounds of the invention are given in the table which follows:

Compound

| $R_7$ | X | Dose (mg/kg) | Decrease in BP (mm Hg) | Duration (Mins) |
|---|---|---|---|---|
| CON⟨O⟩ | — | 1 | 32 | 45 |
| COCH$_2$N⟨⟩ | HCl | 1 | 30 | 90 |
| COCH$_2$N⟨N—CH$_3$⟩ | HCl | 1 | 40 | >120 |
| COCH$_2$N⟨⟩ | HCl | 1 | 40 | 90 |
| COCH$_2$N(C$_2$H$_5$)$_2$ | HCl | 1 | 36 | >60 |

The invention is illustrated, but not restricted, by the examples which follow.

EXAMPLE 1

1α,7β-Diacetoxy-8,13-epoxy-9α-hydroxylabda-5,14-dien-11-one

Freshly distilled thionyl chloride (1.2 ml) was added at 0° C. to a stirred mixture of 1α,7β-diacetoxy-6η,9α-dihydroxy-8,13-epoxylabda-14-en-11-one (5.0 g; 11.06 mmol), dry dichloromethane (200 ml) and dry pyridine (2.5 ml, 30.9 mmol). The stirring was continued at 0° C. for a further half hour and at room temperature for 18 hours.

The reaction mixture was poured onto ice. The organic layer was separated off and washed with water, 10% strength HCl and 1% strength aqueous sodium bicarbonate solution, followed by water, dried over anhydrous sodium sulfate and concentrated. The residue was dissolved in a mixture of ethyl acetate:acetonitrile (9:1) and filtered through florosil (60–100 mesh). The filtrate was concentrated, and the residue was crystallized from ethyl acetate/petroleum ether. Yield 80.2%. Melting point 190°–192° C.

EXAMPLE 2

8,13-Epoxy-1α,9α,7β-trihydroxylabda-5,14-dien-11-one

Sodium hydroxide (1.03 g, 25.75 mmol) in water (30 ml) was added at room temperature to a stirred solution of 1α,7β-diacetoxy-8,13-epoxy-9α-hydroxylabda-5,14-dien-11-one (3.13 g, 7.21 mmol) in methanol (150 ml). The stirring was maintained for a further 3 hours, and the reaction mixture was cooled in an ice/salt bath. The crystalline compound separated out. The crystals were filtered off and dissolved in ethyl acetate. The organic layer was washed with 10% strength aqueous HCl followed by water, dried over anhydrous sodium sulfate and concentrated. The residue was crystallized from ethyl acetate/petroleum ether. Yield 95.78%. Melting point 182°–183° C.

EXAMPLE 3

7β-Chloroacetoxy-1α,9α-dihydroxy-8,13-epoxylabda-5,14-en-11-one

Chloroacetyl chloride (0.38 ml, 4.77 mmol) was added to a cooled, stirred solution of 8,13-epoxy-1α,7β,9α-trihydroxylabda-5,14-dien-11-one (1.5 g, 4.29 mmol) in dry dichloromethane (200 ml) and dry pyridine (1.0 ml). The stirring was continued at 0° C. for one hour and then at room temperature for a further hour. A second aliquot of chloroacetyl chloride (0.1 ml, 1.26 mmol) was added to the reaction mixture, and the stirring was continued for an additional 2 hours. The reaction mixture was diluted with chloroform, and the organic layer was separated off, washed with 10% strength HCl followed by water, dried over anhydrous sodium sulfate and concentrated. The residue was used without purification in the next stage. Yield 97.38%.

EXAMPLE 4

1α,7β-Di-2-bromopropionyloxy-8,13-epoxy-9α-hydroxylabda-5,14-dien-11-one

2-Bromopropionyl bromide (0.56 ml, 5.35 mmol) was added to an ice-cooled, stirred mixture of 8,13-epoxy-1α,7β,9α-trihydroxylabda-5,14-dien-11-one (0.85 g, 2.43 mmol), pyridine (0.5 ml, 6.18 mmol) and dichloromethane (50 ml). The reaction mixture was stirred at room temperature for half an hour. A second aliquot of 2-bromopropionyl bromide (0.56 ml, 5.35 mmol) was added to the reaction mixture, and the stirring was continued at room temperature for a further 6 hours. The reaction mixture was concentrated in vacuo. The residue was extracted with dichloromethane. The organic layer was separated off, washed with 10% strength HCl and water, followed by brine, and concentrated, and the residue was used without further purification in the next stage.

EXAMPLE 5

1α,9α-Dihydroxy-8,13-epoxy-7β-morpholinoacetoxylabda-5,14-dien-11-one

A mixture of 7β-chloroacetoxy-1α,9α-dihydroxy-8,13-epoxylabda-5,14-dien-11-one (0.85 g, 2.0 mmol) and morpholine (10 ml) was stirred at room temperature for 10 min. The reaction mixture was concentrated in vacuo, and the residue was extracted with ethyl acetate. The organic layer was washed with brine and dried over anhydrous sodium sulfate and concentrated. The residue was crystallized from chloroform/petroleum ether, yield 56.3%.

Melting point 164°–166° C.

The following compounds were prepared in a similar manner. The first eleven compounds were converted by treatment with ethereal HCl into the corresponding hydrochlorides.

1. 1α,9α-Dihydroxy-7β-dimethylaminoacetoxy-8,13-epoxylabda-5,14-dien-11-one, m.p. 208°–210° C.
2. 7β-Diethylaminoacetoxy-1α,9α-dihydroxy-8,13-epoxylabda-5,14-dien-11-one, m.p. 169°–170° C.
3. 1α,9α-Dihydroxy-8,13-epoxy-7β-pyrrolidinoacetoxylabda-5,14-dien-11-one, m.p. 206°–208° C.
4. 1α,9α-Dihydroxy-8,13-epoxy-7β-piperidinoacetoxylabda-5,14-dien-11-one.
5. 1α,9α-Dihydroxy-8,13-epoxy-7β-homopiperidinoacetoxylabda-5,14-dien-11-one, m.p. 154°–155° C.
6. 1α,9α-Dihydroxy-8,13-epoxy-7β-morpholinoacetoxylabda-5 14-dien-11-one, m.p. 164°–166° C.
7. 1α,9α-Dihydroxy-8,13-epoxy-7β-N-methylpiperazinoacetoxylabda-5,14-dien-11-one, m.p. 219°–220° C.
8. 1α,9α-Dihydroxy-8,13-epoxy-7β-thiomorpholinoacetoxylabda-5,14-dien-11-one, m.p. 157°–158° C.
9. 1α,9α-Dihydroxy-8,13-epoxy-7β-(4-methylpiperidinoacetoxy)labda-5,14-dien-11-one, m.p. 204°–205° C.
10. 1α,9α-Dihydroxy-8,13-epoxy-7β-(3-methylpiperidinoacetoxy)labda-5,14-dien-11-one, m.p. 179°–181° C.
11. 1α,9α-Dihydroxy-8,13-epoxy-7β-(4-(4-hydroxy-4-phenyl)piperidinoacetoxy)labda-5,14-dien-11-one, m.p. 165°–166° C.
12. 1α,9α-Dihydroxy-7β-(2,6-dimethylaminomorpholinoacetoxy)-8,13-epoxylabda-5,14-dien-11-one, m.p. 191°–192° C.
13. 1α,9α-Dihydroxy-7β-(4-N,N-dimethylaminobutyryloxy)8,13-epoxylabda-5,14-dien-11-one, m.p. 177°–178° C.
14. 1α,9α-Dihydroxy-7β-(4-diethylaminobutyryloxy)-8,13-epoxylabda-5,14-dien-11-one, m.p. 149°–150° C.
15. 1α,9α-Dihydroxy-8,13-epoxy-7β-(4-piperidinobutyryloxy)labda-5,14-dien-11-one, m.p. 185°–186° C.
16. 1α,9α-Dihydroxy-8,13-epoxy-7β-(4-morpholinobutyryloxy)labda-5,14-dien-11-one, m.p. 183°–184° C.
17. 1α,9α-Dihydroxy-8,13-epoxy-7β-(4-N-methylpiperazinobutyryloxy)labda-5,14-dien-11-one, m.p. 196°–197° C.
18. 1α,9α-Dihydroxy-8,13-epoxy-7β-[4-(4-hydroxy-4phenyl)piperidino)butyryloxy]labda-5,14-dien-11-one, m.p. 132°–133° C.
19. 1α,9α-Dihydroxy-7β-(5-dimethylaminovaleryloxy)-8,13-epoxylabda-5,14-dien-11-one, m.p. 172°–173° C.
20. 1α,9α-Dihydroxy-8,13-epoxy-7β-(5-piperidinovaleryloxy)labda-5,14-dien-11-one, m.p. 166°–169° C.
21. 1α,9α-Dihydroxy-8,13-epoxy-7β-(5-morpholinovaleryloxy)labda-5,14-dien-11-one, m.p. 168°–169° C.
22. 1α,9α-Dihydroxy-8,13-epoxy-7β-(5-N-methylpiperazinovaleryloxy)labda-5,14-dien-11-one, m.p. 161°–162° C.
23. 1α,9α-Dihydroxy-8,13-epoxy-7β-(2-piperidinopropionyloxy)labda-5,14-dien-11-one, m.p. 199°–203° C.

EXAMPLE 6

1α,9α-Dihydroxy-8,13-epoxy-7β-(2R,3-0-isopropylideneglyceroyloxy)labda-5,14-dien-11-one 8,13-Epoxy-1α,7β,9α-trihydroxylabda-5,14-dien-11-one (1.0 g, 2.86 mmol) in dry ethyl acetate (25 ml) was added to a cooled mixture of 4-N,N-dimethylaminopyridine (0.7 g, 5.73 mmol), dicyclohexylcarbodiimide (1.85 g, 8.97 mmol) and 2R,3-0-isopropylideneglyceric acid (0.926 g, 6.34 mmol) in dry ethyl acetate (50 ml). The reaction mixture was left to stand at room temperature for 16 hours. Acetic acid (0.5 ml, 8.73 mmol) was then added to the reaction mixture, which was stirred at room temperature for 15 min. The reaction mixture was diluted with further ethyl acetate, filtered, and the filtrate was washed with a cooled solution of aqueous sodium bicarbonate solution, followed by brine. The organic layer was dried over anhydrous sodium sulfate and concentrated. The residue was purified by flash column chromatography using ethyl acetate:diisopropyl ether:petroleum ether (8:46:46) as eluent. Pure fractions were combined and evaporated, and the product was crystallized from n-pentane, yield 22.6%, melting point 151°–153° C. The compound 1α9α,-Dihydroxy-8,13-epoxy-7β-(2S 3-0-isopropylidino-propionyloxy-labd-5,14-dien-11-one was prepared similarly using 2S,3-0-isopropylidinopropionic acid in place of 2R,3-0-isopropylidinopropionic acid.

EXAMPLE 7

1α,9α-Dihydroxy-8,13-epoxy-7β-(2R,3-dihydroxypropionyloxy)labda-5,14-dien-11-one p-Toluenesulfonic acid monohydrate (0.384 g, 2.02 mmol) was added under an $N_2$ atmosphere to a stirred solution of 1α,9α-dihydroxy-8,13-epoxy-7β-(2R,3-0-isopropylideneglyceroyloxy)labda-5,14-dien-11-one (0.52 g, 1.09 mmol) in methanol (24 ml). The reaction mixture was stirred at room temperature for 1.5 hours and concentrated in vacuo at a temperature <40° C. The residue was extracted with ethyl acetate. The organic layer was washed with 10% strength aqueous sodium bicarbonate solution followed by water, dried over anhydrous sodium sulfate and concentrated. The residue was purified by flash column chromatography using ethyl acetate:diisopropyl ether (3:7) as eluent. Pure fractions were combined and concentrated, and the residue was crystallized from ethyl acetate/petroleum ether. Yield 79.8%, melting point 182°–184° C.

The compound 1α,9α-Dihydroxy-8,13-epoxy-7β-(2S,3-dihydroxypropionyloxy)-labd-5,14-dien-11-one quasihydrate, m.p. 215° C. was prepared in a similar manner.

EXAMPLE 8

7β-Acetoxy-1α-t-butyldimethylsilyloxy-8,13-epoxy-9α-hydroxylabda-5,14-dien-11-one Thionyl chloride (0.73 ml, 10 mmol) was added to an ice-cooled, stirred mixture of 7β-acetoxy-1α-t-butyldimethylsilyloxy-6β,9α-dihydroxy-8,13-epoxylabd-14-en-11-one (3.5 g, 6.68 mmol) in methylene chloride (200 ml) and pyridine (1.61 ml, 19.9 mmol). The reaction mixture was stirred at 28° C. overnight and was washed with 10% strength aqueous HCl followed by saturated sodium bicarbonate solution and water. The organic layer was dried over anhydrous sodium sulfate and concentrated. The product was obtained as an oil in 96% yield.

EXAMPLE 9

1α-t-Butyldimethylsilyloxy-7β,9α-dihydroxy-8,13-epoxylabda-5,14-dien-11-one

Sodium hydroxide (0.54 g, 13.5 mmol) in water (30 ml) was added to a stirred solution of 7β-acetoxy-1α-t-butyldimethylsilyloxy-8,13-epoxy-9α-hydroxylabda-5,14-dien-11-one (3.4 g, 6.71 mmol) in methanol (90 ml). The reaction mixture was stirred at 28° C. for 45 min, and was concentrated in vacuo to one quarter of its volume in order to remove methanol. The residue was extracted with ethyl acetate. The organic layer was washed with water, dried over anhydrous sodium sulfate and concentrated. The residue was purified by flash column chromatography using ethyl acetate:petroleum ether (2:8) as eluent, melting point 104°–105° C.

EXAMPLE 10

1α-t-Butyldimethylsilyloxy-8,13-epoxy-9α-hydroxy-7β-piperidinecarbonyloxylabda-5,14-dien-11-one 1,1'-Carbonyldiimidazole (0.419 g, 2.58 mmol) was added under an $N_2$ atmosphere to a stirred solution of 1α-t-butyldimethylsilyloxy-7β,9α-dihydroxy-8,13-epoxylabda-5,14-dien-11-one (1.0 g, 2.16 mmol) in dry ethyl acetate (25 ml). The reaction mixture was stirred at room temperature overnight and then a second aliquot of 1,1'-carbonyldiimidazole (0.419 g, 2.58 mmol) was added to the reaction mixture, which was stirred for a further 12 hours. Piperidine (1 ml) was added to this reaction mixture, and stirring was continued at room temperature for one hour. It was diluted with further ethyl acetate and washed with water, dried over anhydrous sodium sulfate and concentrated.

EXAMPLE 11

1α,9α-Dihydroxy-8,13-epoxy-7β-piperidinocarbonyloxylabda-5,14-diene-11-one

Tetrabutylammonium fluoride trihydrate (0.484 g, 1.53 mmol) was added at 0° C. to a stirred Solution of 1α-t-butyldimethylsilyloxy-8,13-epoxy-9α-hydroxy-7β-piperidinocarbonyloxylabda-5,14-dien-11-one (0.4 g, 0.73 mmol) in dry tetrahydrofuran (10 ml). Stirring was continued for one hour. The reaction mixture was concentrated in vacuo. The residue was extracted with ethyl acetate, and the organic layer was washed with water, dried over anhydrous sodium sulfate and concentrated. The residue was purified by flash column chromatography using ethyl acetate:petroleum ether (3:7) as eluent, and the product was crystallized from ethyl acetate/petroleum ether.

Yield 84.3%, melting point 199°–200° C.

The compounds in Table II were prepared by the methods described in Example 10 and Example 11.

EXAMPLE 12

7β-Acryloyloxy-1α,9α-dihydroxy-8,13-epoxylabda-5,14-dien-11-one

Using acrylic acid in place of 2R,3-0-isopropylideneglyceric acid in the process described in Example 6 the compound 7β-acryloyloxy-1α,9α-dihydroxy-8,13-epoxylabda-5,14-dien-11-one was prepared, melting point 142°–143° C.

Similarly following compounds were prepared starting from 1α,9α-Dihydroxy-8,13-epoxy-7β-(hydroxy)acetoxy-labd-5,14-dien-11-one and 1α-t Butyldimethylsilyloxy-8,13-epoxy-7β-(hydroxy)acetoxy-9-hydroxy-labd-5,14-dien-11-one respectively. 7β-(Acryloyloxy)acetoxy-1α,9α-dihydroxy-8,13-epoxylabd-5,14-dien-11-one.

7β-(Acryloyloxy)acetoxy-1α-t-butyldimethylsilyloxy-8,13-epoxy-9α-hydroxy-labd-5,14-dien-11-one.

EXAMPLE 13

1α,9α-Dihydroxy-8,13-epoxy-7β-(3-piperidinopropionyloxy)labda-5,14-dien-11-one

A mixture of piperidine (5 ml) and 7β-acryloyloxy-1α,9α-dihydroxy-8,13-epoxylabda-5,14-dien-11-one (0.12 g, 0.3 mmol) was heated at 70° C. for 45 minutes. The reaction mixture was concentrated in vacuo. The residue was extracted with ethyl acetate, and the organic layer was washed with brine, dried over anhydrous sodium sulfate and concentrated. The residue was crystallized from chloroform:petroleum ether. Yield 91%. Melting point 169°–170° C. The following compounds were prepared in a similar manner.

1. 1α,9α-Dihydroxy-7β-(β-dimethylaminopropionyloxy)-8,13-epoxylabda-5,14-dien-11-one, melting point 113°–164° C., using dimethylamine in toluene in place of piperidine pure).
2. 7β-(3-Diethylaminopropionyloxy)-1α,9α-dihydroxy-8,13-epoxylabda-5,14-dien-11-one, melting point 153°–154° C.
3. 1α,9α-Dihydroxy-8,13-epoxy-7β-(3-morpholinopropionyloxy)labda-5,14-dien-11-one, melting point 168°–169° C.
4. 1α,9α-Dihydroxy-8,13-epoxy-7β-(3-N-methylpiperazinopropionyloxy)labda-5,14-dien-11-one, melting point 154°–155° C.
5. 1α,9α-Dihydroxy-8,13-epoxy-7β-[3-(4-(4-hydroxyphenyl)piperidino)propionyloxy]labda-5,14-dien-11-one, melting point 187°–188° C.
6. 1α,9α-Dihydroxy-7β-(3-N,N-dimethylaminopropionyloxy)acetoxy-8,13-epoxy-labd-5,14-dien-11-one.
7. 1α, 9α-Dihydroxy-8,13-epoxy-7β-(3-morpholinopropionyloxy)acetoxy-labd-5,14-dien-11-one.
8. 1α,9α-Dihydroxy-8,13-epoxy-7β-(3-N-methylpiperazino-propionyloxy)-acetoxy-labd-5,14-dien-11-one.

EXAMPLE 14

1α-t-Butyldimethylsilyloxy-8,13-epoxy-9α-hydroxy-7βhydroxyacetoxylabda-5,14-dien-11-one Bromoacetyl bromide (2.7 ml) was added to 1α-t-butyldimethylsilyloxy-7β,9α-dihydroxy-8,13-epoxylabda-5,14-dien-11-one (11.0 g) by the process described in Example 3. The residue from the working up of the reaction was dissolved in hexamethylphosphoramide (40 ml) and treated at room temperature with sodium formate (1.8 g). The reaction mixture was stirred for 6 hours and left to stand at room temperature for 48 hours. The reaction mixture was then diluted with chloroform, and the chloroform solution was passed through a column of neutral alumina (1250 g), extracting with chloroform (2 liters) followed by chloroform:methanol (9:1, 4 liters). The fractions containing the compound were combined and concentrated. The resulting oil which remained was further purified by flash chromatography using ethyl acetate: petroleum ether (2:8) as eluent (yield 10.0 g, 81%).

The following compounds were prepared in a similar manner.

The compound 1α,9α-dihydroxy-8,13-epoxy-7β-hydroxyacetoxylabda-5,14-dien-11-one, melting point 156° C., was obtained from 8,13-epoxy-1α,7β,9α-trihydroxylabda-5,14-dien-11-one.

In a similar manner, the compound 1α,9α-dihydroxy-8,13-epoxy-7β-formyloxyacetoxylabda-5,14-dien-11-one was obtained from 8,13-epoxy-1α,7β,9α-trihydroxylabda-5,14-dien-11-one.

EXAMPLE 15

1α-t-Butyldimethylsilyloxy-7β-chloroacetoxyacetoxy-8,13-epoxy-9α-hydroxylabda-5,14-dien-11-one The compound 1α-t-butyldimethylsilyloxy-7β-chloroacetoxyacetoxy-8,13-epoxy-9α-hydroxylabda-5,14-dien-11-one was obtained in 59% yield, melting point 143°–145° C., by the process described in Example 6, using 1α-t-butyldimethylsilyloxy-8,13-epoxy-7β-hydroxyacetoxy-9 α-hydroxylabda-5,14-dien-11-one and chloroacetic acid. The following compounds were prepared in a similar manner: 7β-Acryloyloxy-1α-t-butyldimethylsilyloxy-8,13-epoxy-9α-hydroxylabda-5,14-dien-11-one was prepared from 1α-t-butyldimethylsilyloxy-8,13-epoxy-7β,9α-dihydroxylabda-5,14-dien-11-one and acrylic acid. 7β-Acryloyloxyacetoxy-1α-t-butyldimethylsilyloxy-8,13-epoxy-9α-hydroxylabda-5,14-dien-11-one was prepared from 1α-t-butyldimethylsilyloxy-8,13-epoxy-7β-hydroxyacetoxy-9α-hydroxylabda-5,14-dien-11-one and acrylic acid.

EXAMPLE 16

1α,9α-Dihydroxy-8,13-epoxy-7β-piperidinoacetoxyacetoxylabda-5,14-dien-11-one

Piperidine (0.5 ml) was reacted for 1.5 hours with 1α-t-butyldimethylsilyloxy-7β-chloroacetoxyacetoxy-8,13-epoxy-9α-hydroxylabda-5,14-dien-11-one (0.5 g), dissolved in dichloromethane (20 ml). The residue from the working up of the reaction was treated as described in Example 11 with tetrabutylammonium fluoride (0.85 ml, 1M solution) in tetrahydrofuran. The reaction was complete after 20 minutes. The resulting product was purified by flash chromatography using acetonitrile:-chloroform:diisopropyl ether:triethylamine (2:50:47:1) as eluent. Yield 0.240 g, 54%, melting point 108°–110° C. The compound 1α,9α-dihydroxy-8,13-epoxy-7β-morpholinoacetoxyacetoxylabda-5,14-dien-11-one, melting point 145°–146° C., was prepared in a similar manner by use of morpholine in place of piperidine.

Similarly, following compounds were prepared using appropriate amines:

1α,9α-Dihydroxy-7β-(N,N-dimethylaminoacetoxy)acetoxy-8,13-epoxy-labd-5,14-dien-11-one.

7β-(N,N-Diethylaminoacetoxy)acetoxy-1α,9α-dihydroxy-8,13-epoxy-labd-5,14-dien-11-one.

1α,9α-Dihydroxy-8,13-epoxy-7β-(morpholinoacetoxy)acetoxy-labd-5,14-dien-11-one, m.p. 145°–146° C.

1α,9α-Dihydroxy-7β-(2,6-dimethylmorpholinoacetoxy)acetoxy-8,13-epoxy-labd-5,14-dien-11-one.

1α,9α-Dihydroxy-8,13-epoxy-7β-(4-hydroxy-4-phenylpiperidinoacetoxy)acetoxy-labd-5,14-dien-11-one.

EXAMPLE 17

7β-Amino-carbonyloxy-1α,9α-dihydroxy-8,13-epoxylabd-5,14-dien-11-one

TFA (0.34 ml, 4,4 mmol) was added to a stirred mixture of potassium cyanate (0.34 g, 4.2 mmol) and 1α-t-butyldimethylsilyloxy-7β,9α-dihydroxy-8,13-epoxy- 5,14-dien-11-one (1.3 g, 2.69 mmol) in dry toluene (25 ml). Stirring is continued for 12 hrs. The reaction mixture was diluted with water and extracted with ethyl acetate. The organic layer was washed with brine, dried over anhydrous sodium sulphate and concentrated. The residue was purified by flash chromatography using ethyl acetate:pet. ether (4:6) as eluant gave 7β-Aminocarbonyloxy-1α-t-butyldimethylsilyloxy-8,13-epoxy-9α-hydroxylabd-5,14-dien-11-one (0.26 g) and 7β-Aminocarbonyloxy-1α,9α-dihydroxy-8,13-epoxy-5,14-dien-11-one (0.023 g). The former compound was deprotected using the procedure reported in Example 11. Yield 0.182 g, m.p. 233°–234° C.

EXAMPLE 18

1α,9α-Dihydroxy-8,13-epoxy-7β-morpholinoacetoxy-labd-5,14-dien-11-one hydrochloride Etheral HCl was added to an ice cooled solution of 1α,9α-Dihydroxy-8,13-epoxy-7β-morpholinoacetoxy-labd-5,14-dien-11-one (0.3 g) in methanol (10 ml) till it reached to pH 2. A precipitate separates out which was filtered and washed with dry ether. The residue was recrystallized with methanol:diethyl ether. Yield 90%, m.p. 192°–194° C. (decomposed). Similarly the following compounds were prepared.

1. 1α,9α-Dihydroxy-7β-dimethylaminoacetoxy-8,13-epoxy-labd-5,14-dien-11one hydrochloride, m.p. 243° C.
2. 7β-Diethylaminoacetoxy-1α,9α-dihydroxy-8,13-epoxy-labd-5,14-dien-11-one hydrochloride, m.p. 210°–211° C.
3. 1α,9α-Dihydroxy-8,13-epoxy-7β-pyrrolidinoacetoxy-labd-5,14-dien-11-one hydrochloride, m.p. 220°–221° C.
4. 1α,9α-Dihydroxy-8,13-epoxy-7β-piperidinoacetoxy-labd-5,14-dien-11-one hydrochloride, m.p. 227°–228° C.
5. 1α,9α-Dihydroxy-8,13-epoxy-7β-homopiperidinoacetoxy-labd-5,14-dien-11-one hydrochloride, m.p. 215°–216° C.
6. 1α,9α-Dihydroxy-8,13-epoxy-7β-N-methylpiperazinoacetoxy-labd-5,14-dien-11-one dihydrochloride hydrate, m.p. 220°–223° C.
7. 1α,9α-Dihydroxy-8,13-epoxy-7β-thiomorpholinoacetoxy-labd-5,14-dien-11-one hydrochloride; m.p. 203°–204° C.
8. 1α,9α-Dihydroxy-8,13-epoxy-7β-(4'-methylpiperidinoacetoxy)-labd-5,14-dien-11-one hydrochloride, m.p. 228°–230° C.
9. 1α,9α-Dihydroxy-8,13-epoxy-7β-(3'-methylpiperidinoacetoxy)labd-5,14-dien-11-one hydrochloride hemihydrate, m.p. 219°–220° C.
10. 1α,9α-Dihydroxy-8,13-epoxy-7β-(4-hydroxy-4-phenylpiperidino)acetoxy-labd-5,14-dien-11-one hydrochloride hydrate, m.p. 194°–195° C.
11. 1α,9α-Dihydroxy-8,13-epoxy-7β-(2'-piperidino-propionyloxy)-labd-5,14-dien-11-one hydrochloride, m.p. 225°–226° C.
12. 1α,9α-Dihydroxy-8,13-epoxy-7β-(piperidinoacetoxy)acetoxy-labd-5,14-dien-11-one hydrochloride, m.p. 217°–219° C.
13. 1α,9α-Dihydroxy-8,13-epoxy-7β-(morpholinoacetoxy)acetoxy-labd-5,14-dien-11-one hydrochloride, m.p. 192°–194° C. (decomposition).
14. 1α,9α-Dihydroxy-7β-(N,N-dimethylaminoacetoxy)acetoxy-8,13-epoxy-labd-5,14-dien-11-one hydrochloride, m.p. 209° C.
15. 7β-(N,N-Diethylaminoacetoxy)-1α,9α-dihydroxy-8,13-epoxy-labd-5,14-dien-11-one hydrochloride hydrate, m.p. 130°–133° C.
16. 1α,9α-Dihydroxy-7β-(2,6-dimethylmorpholinoacetoxy)acetoxy-8,13-epoxy-labd-5,14-dien-11-one hydrochloride hydrate, m.p. 138°–140° C.
17. 1α,9α-Dihydroxy-8,13-epoxy-7β-(4-hydroxy-4-phenylpiperidinoacetoxy)acetoxy-labd-5,14-dien-11one hydrochloride hemihydrate, m.p. 157°–160° C.
18. 1α,9α-Dihydroxy-8,13-epoxy-7β-(N-methylpiperazino acetoxy)acetoxy-labd-5,14-dien-11-one dihydrochloridedehydrate, m.p. 177°–180° C.
19. 1α,9α-Dihydroxy-7β-(3-N,N-dimethylaminopropionyloxy)acetoxy-8,13-epoxy-labd-5,14-dien-11-one hydrochloride hemihydrate, m.p. 178° C.
20. 1α,9α-Dihydroxy-8,13-epoxy-7β-(3-piperidinopropionyloxy)acetoxy-labd-5,14-dien-11-one hydrochloride hydrate, m.p. 171° C.
21. 1α,9α-Dihydroxy-8,13-epoxy-7β-(3-morpholinopropionyloxy)acetoxy-labd-5,14-dien-11-one hydrochloride, m.p. 189°–190° C.
22. 1α,9α-Dihydroxy-8,13-epoxy-7β-(3-N-methylpiperazinopropionyloxy)acetoxy-labd-5,14-dien-11-one dihydrochloride hydrate, m.p. 230° C.

What is claimed is:

1. A compound of the formula I:

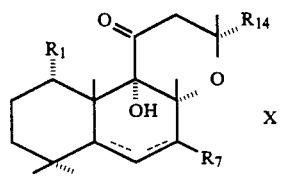

in which $R_1$ represents hydroxyl or $C_1$–$C_{18}$-alkanoyloxy,
$R_7$ is a radical of the formula II:

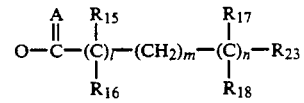

in which l represents 0 or an integer from 1 to 4,
m and n represent 0,
A represents oxygen or sulfur,
$R_{15}$ to $R_{18}$ are each hydrogen,
$R_{23}$ is a group of the formula $NR_{24}R_{25}$,
in which $R_{24}$ and $R_{25}$ represent,
when they are identical, hydrogen, $C_1$–$C_6$-alkyl, hydroxy-$C_1$–$C_6$-alkyl, carboxy-$C_1$–$C_6$-alkyl, carb-$C_1$–$C_6$-alkoxy-$C_1$–$C_6$-alkyl, phenyl unsubstituted or substituted by halogen, $C_1$–$C_3$-alkyl, $C_1$–$C_3$-alkoxy, nitro or trifluoromethyl, phenyl-$C_1$–$C_6$-alkyl unsubstituted or substituted in the phenyl moiety by halogen, $C_1$–$C_3$-alkyl, $C_1$–$C_3$-alkoxy, nitro or trifluoromethyl, or,
when they are not identical, $R_{24}$ represents hydrogen or $C_1$–$C_6$-alkyl,
when $R_{24}$ represents hydrogen, $R_{25}$ represents $C_1$–$C_6$-alkyl, hydroxy-$C_1$–$C_6$-alkyl, $C_3$–$C_7$-cycloalkyl, phenyl-$C_1$–$C_6$-alkyl unsubstituted or substituted in the phenyl moiety by halogen, $C_1$–$C_3$-alkyl, $C_1$–$C_3$-alkoxy, nitro or trifluoromethyl, phenyl unsubstituted or substituted by halogen, $C_1$–$C_3$-alkyl, $C_1$–$C_3$-alkoxy, nitro or trifluoromethyl, amino, di-$C_1$–$C_6$-alkylamino, $C_1$–$C_6$-alkylamino, phenylamino unsubstituted or substituted in the phenyl moiety by halogen, $C_1$–$C_3$-alkyl, $C_1$–$C_3$-alkoxy, nitro or trifluoromethyl, phenylamino-$C_1$–$C_6$-alkyl unsubstituted or substituted in the phenyl moiety by halogen, $C_1$–$C_3$-alkyl, $C_1$–$C_3$-alkoxy, nitro or trifluoromethyl, hydroxyl, mercapto, $C_1$–$C_6$-alkanoyloxy, $C_2$–$C_6$-alkenoyloxy, $C_3$–$C_6$-alkynoyloxy, benzoyloxy unsubstituted or substituted in the phenyl moiety by halogen, $C_1$–$C_3$-alkyl, $C_1$–$C_3$-alkoxy, nitro or trifluoromethyl, phenyl-$C_1$–$C_6$-alkanoyloxy unsubstituted or substituted in the phenyl moiety by halogen, $C_1$–$C_3$-alkyl, $C_1$–$C_3$-alkoxy, nitro or trifluoromethyl, pyridine-3-carbonyloxy unsubstituted or substituted in the pyridine moiety by halogen, $C_1$–$C_3$-alkyl, $C_1$–$C_3$-alkoxy, nitro or trifluoromethyl, $C_1$–$C_6$-alkanoyl, $C_2$–$C_6$-alkenoyl, $C_3$–$C_6$-alkynoyl, benzoyl unsubstituted or substituted in the phenyl moiety by halogen, $C_1$–$C_3$-alkyl, $C_1$–$C_3$-alkoxy, nitro or trifluoromethyl, phenyl-$C_1$–$C_6$-alkanoyl unsubstituted or substituted in the phenyl moiety by halogen, $C_1$–$C_3$-alkyl, $C_1$–$C_3$-alkoxy, nitro or trifluoromethyl, pyridine-3-carbonyl unsubstituted or substituted in the pyridine moiety by halogen, $C_1$–$C_3$-alkyl, $C_1$–$C_3$-alkoxy, nitro or trifluoromethyl, carbamoyl, carboxy-$C_1$–$C_6$-alkyl, carb-$C_1$–$C_6$-alkoxy-$C_1$–$C_6$-alkyl, di-$C_1$–$C_6$-alkylamino-$C_1$–$C_6$-alkyl, or when $R_{24}$ represents $C_1$–$C_6$-alkyl, $R_{25}$ represents hydroxy-$C_1$–$C_6$-alkyl, carboxy-$C_1$–$C_6$-alkyl, carb-$C_1$–$C_6$-alkoxy-$C_1$–$C_6$-alkyl, $C_3$–$C_7$-cycloalkyl, phenyl unsubstituted or substituted by halogen, $C_1$–$C_3$-alkyl, $C_1$–$C_3$-alkoxy, nitro or trifluoromethyl, phenyl-$C_1$–$C_6$-alkyl unsubstituted or substituted in the phenyl moiety by halogen, $C_1$–$C_3$-alkyl, $C_1$–$C_3$-alkoxy, nitro or trifluoromethyl, di-$C_1$–$C_6$-alkylamino-$C_1$–$C_6$-alkyl, or $R_{24}$ and $R_{25}$ together represent with the nitrogen atom to which they are attached a piperidine, homopiperidine, pyrrolidine, morpholine, piperazine, thiomorpholine, imidazole or theophylline radical which can be substituted by $C_1$–$C_6$-alkyl, phenyl unsubstituted or substituted by halogen, $C_1$–$C_3$-alkyl, $C_1$–$C_3$-alkoxy, nitro or trifluoromethyl, $R_{14}$ represents vinyl, ethyl, cyclopropyl, —CH(OH)—CH$_2$OH, CH$_2$OH or

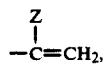

in which Z represents chlorine, bromine, or fluorine,

X is present or absent, and when X is present, the formula I represents a pharmacologically utilizable salt, and the dotted lines represent a double bond present in either the 5,6- or the 6,7-position.

2. A compound of the formula I as claimed in claim 1, in which
$R_7$ represents a radical of the formula II':

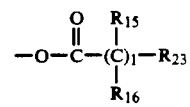

in which $R_{15}$, $R_{16}$, $R_{23}$ and 1, are as defined in claim 1.

3. A compound of the formula I as claimed in claim 1, in which
$R_1$ represents hydroxyl or $C_1$–$C_{18}$-alkanoyloxy, and
$R_7$ represents a radical of the formula II'':

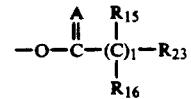

A, $R_{15}$, $R_{16}$, $R_{23}$ and 1 are as defined in claim 1,
with the proviso that a double bond is present in the 5,6-position.

4. A compound of the formula I as claimed in claim 1, in which
$R_1$ represents hydroxyl,
$R_7$ represents a radical of the formula II':

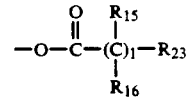

in which
$R_{15}$, $R_{16}$, $R_{23}$ and 1 are as defined in claim 1,
and a double bond is present in the 5,6-position.

5. A compound of the formula I as claimed in claim 1 in which $R_{14}$ represents vinyl.

6. A compound as claimed in claim 1, which is 1α,9α-dihydroxy-7β-(4, N,N-dimethylaminobutyryloxy)-8,13-epoxylabda-5,14-dien-11-one.

7. A compound as claimed in claim 1, which is 1α,9α-dihydroxy-7β-(N-methylaminocarbonyloxy)-8,13-epoxylabda-5,14-dien-11-one.

8. A pharmaceutical composition comprising a compound of the formula I as claimed in claim 1 in an amount effective to exhibit inotropic activity or antihypertensive activity or for lowering intraocular pressure, together with a pharmaceutically acceptable carrier.

9. A method of treating a patient which comprises administering to the patient a compound of the formula I as defined in claim 1 in an amount effective to exhibit positive inotropic activity.

10. A method of lowering blood pressure in a patient which comprises administering to the patient an effective amount of a compound of the formula I as claimed in claim 1.

11. A method of lowering intraocular pressure in a patient which comprises administering to the patient an effective amount of a compound of the formula I as claimed in claim 1.

* * * * *

UNITED STATES PATENT AND TRADEMARK OFFICE
CERTIFICATE OF CORRECTION

PATENT NO. : 5,252,598
DATED : October 12, 1993
INVENTOR(S) : Yatendra Khandelwal et al.

It is certified that error appears in the above-indentified patent and that said Letters Patent is hereby corrected as shown below:

Claim 3, column 32, line 22, before "A," insert --in which--.

Signed and Sealed this

Sixth Day of September, 1994

Attest:

BRUCE LEHMAN

*Attesting Officer*  *Commissioner of Patents and Trademarks*